Figure 1:
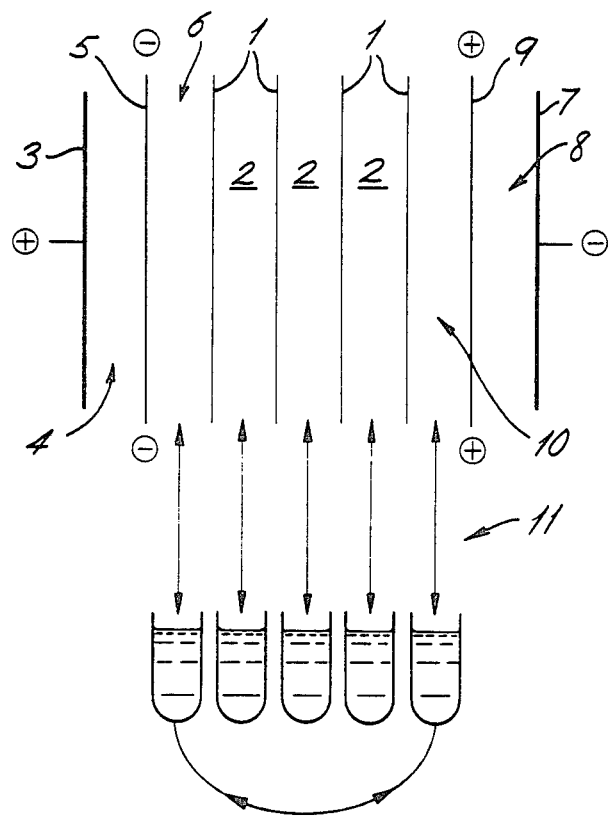

United States Patent [19]

Martin et al.

[11] 4,243,507

[45] Jan. 6, 1981

[54] MEMBRANE ELECTROPHORESIS

[75] Inventors: Archer J. P. Martin, Elstree; Frank Hampson, Lewes, both of England

[73] Assignee: National Research Development Corporation, England

[21] Appl. No.: 12,445

[22] Filed: Feb. 15, 1979

[51] Int. Cl.$^3$ .................... G01N 27/40; G01N 27/26
[52] U.S. Cl. .................... 204/301; 204/180 R; 204/180 P; 204/296; 204/299 R
[58] Field of Search .......... 204/180 G, 180 R, 180 P, 204/301, 296, 299 R

[56] References Cited

U.S. PATENT DOCUMENTS

| | | | |
|---|---|---|---|
| 3,240,692 | 3/1966 | Donnelly | 204/180 P |
| 3,510,417 | 5/1970 | Mizutani et al. | 204/180 P |
| 3,654,125 | 4/1972 | Leitz | 204/301 |
| 3,718,559 | 2/1973 | Wallace | 204/301 X |
| 3,870,617 | 3/1975 | Bourat | 204/301 |
| 3,948,743 | 4/1976 | Monthony et al. | 204/299 R X |

FOREIGN PATENT DOCUMENTS

| | | |
|---|---|---|
| 2638526 | 7/1977 | Fed. Rep. of Germany . |
| 1223635 | 6/1960 | France . |
| 1316726 | 5/1963 | France . |
| 1527883 | 6/1968 | France . |
| 2334951 | 7/1977 | France . |
| 1121449 | 7/1968 | United Kingdom . |
| 1255418 | 12/1971 | United Kingdom . |

Primary Examiner—Arthur C. Prescott
Attorney, Agent, or Firm—Jacobs & Jacobs

[57] ABSTRACT

The separation of substances by membrane electrophoresis using the principle of isoelectric focussing is improved by the use of membranes of known isoelectric point and having buffering capacity. When such membranes are arranged in series of increasing isoelectric point from the anode (+) to the cathode (−) in a pH gradient of increasing pH in the same direction, and each membrane is located between electrolyte zones having pHs respectively lower and higher than its isoelectric point, the tendency for electro-endosmosis to occur during electrophoresis is substantially reduced.

Methods for chemical treatment of agarose and other gel membranes to introduce acidic and basic groups so as to confer buffering power at the isoelectric point are described. These include the attachment of ampholytes to the gel by intermediate chemical linkages. Under varying chemical conditions membranes exhibiting isoelectric properties over a range of pH values can be prepared and specific values predetermined to within narrow limits.

The membranes are used in multicompartment apparatus with separate cooling of individual circulating electrolyte zones and may be in the form of sheet membranes mounted in a nesting configuration one above the next with gravity flow of electrolyte and edge sealing between the membranes. High current and large scale use of the method for preparative as well as analytical purposes are envisaged.

17 Claims, 3 Drawing Figures

MEMBRANE ELECTROPHORESIS

This invention relates to electrophoresis and more particularly to electrophoresis through membranes to effect isoelectric focussing.

Membrane electrophoresis is a known technique and various forms of electrophoresis apparatus have been proposed for both analytical and preparative purposes. These have been reviewed by A. J. P. Martin and R. L. M. Synge in "Advances in Protein Chemistry", Vol. 2, pages 31–38, Academic Press 1945 and R. L. M. Synge in Biochemical Journal 1951 49 643–650. So far, however, no apparatus has been available in which large quantities of material can be treated. Large scale work involves the use of high currents which inevitably generate much heat and therefore requires efficient cooling of the electrolytes for continuous operation. Furthermore, considerable problems exist in connection with membrane stability and performance.

The greatest of such problems is that of electroendosmosis, a term denoting bulk fluid flow through the membranes caused by the presence or acquisition of an electrical charge on the membrane. Not only is it difficult to prepare membranes which are initially free of electric charge but even where this can be achieved it is found that the membranes acquire charge by absorption of ions from the electrolyte during the electrophoretic process. The charged membranes will tend to respond to the applied electric field but because they are not free to move with respect to the electrolyte the effect observed empirically is that of a corresponding movement of electrolyte through the membrane. The consequent flow of bulk electrolyte is unacceptable both because it destroys the stability of the carefully established pH gradient, an essential condition of electrophoresis, and because it causes remixing of the separated species. These effects can totally vitiate the electrophoretic effect.

The basic concept of the present invention is that of an electrophoresis membrane having a known isoelectric point and buffering capacity at its isoelectric point. Such a membrane, the electrophoretic characteristics of which are known and calibrated, has the property that when disposed in a pH gradient encompassing a narrow range about a specific pH, which can be designated as the isoelectric pH, there will be only a very small or virtually no net charge on the membrane. Because of its buffering power, the membrane will remain under stable substantially isoelectric conditions during the electrophoretic process and therefore there will be little or no tendency for electroendosmosis to occur during electrophoresis.

Membranes in accordance with this invention may be obtained by incorporating both positively and negatively charged species into the membrane, notably basic and acidic groups respectively, so as to induce a high density of charge of both signs, an appreciable number of which have a pK close enough, e.g. within about one pH unit, to the isoelectric point to exert buffering power. When such a membrane is placed in contact with an electrolyte of a predetermined known pH there will be minimal net charge on the membrane. The membrane is thus internally buffered at its isoelectric point.

The approach taken by the present invention is based on the realisation that, in order to reduce or eliminate electroendosmosis, the membranes separating the compartments in a multi-compartment isoelectric focussing apparatus should possess the smallest possible or virtually no net charge at the pH prevailing in the pores of the membrane which of course will be for each membrane a value intermediate between the pHs on both sides of it. According to this invention the membranes possess a high density of charges of both signs and of appropriate ionization constant so that the membrane has a high buffering capacity at its isoelectric point and therefore absorption of ions will cause very small effects.

MEMBRANE PREPARATION

The preparation of membranes in accordance with the invention may be carried out with well known and typical membrane-forming materials known to be suitable for electrophoresis purposes. Such materials include gel-forming polymers which are sufficiently chemically reactive to enable the introduction of ionisable radicals i.e. acid groups such as carboxylic, sulphonic, phosphonic groups and nitrogenous basic groups such as amino groups. Typical suitable materials are hydroxylic polymers including cellulose, modified cellulose, cross-linked polyvinyl alcohol and cross-linked polyethylene oxide. Cross-linked polyacrylamide gels suitably chemically modified may also be used. Especially good results have been obtained with agar or agarose gels. Conveniently these may be supported on porous carrier substrates such as filter-paper, cotton or linen cloth, or other suitable web materials to provide adequate strength. Additionally, some cross-linking of the agar or agarose gels is advisable to withstand the chemical reaction conditions necessary for the introduction of ionisable groups as hereinafter described.

The introduction of groups capable of generating negative ions may very conveniently be achieved by carboxyalkylation e.g. by treatment with a suitable salt or derivative of chloracetic acid to introduced the group $-CH_2COOH$. Likewise groups which can give rise to positively charged species may be introduced by amino-alkylation e.g. by treatment with a diethylamino ethyl halide to introduce the group $-CH_2CH_2NEt_2$. In a modification of this method, more complex amino-containing radicals may be chemically combined with the membrane in a step-wise manner by reaction with a linking reagent e.g. epichlorhydrin to introduce a substituent which is further reacted with a suitable amine e.g. diethanolamine. These methods are generally well known in the production of ion exchange and chromatographic materials and their application for the purposes of the present invention is relatively straightforward requiring, however, some experimentation to determine the appropriately mild reaction conditions for use with the relatively delicate membrane structures. It has been found advantageous in practice to develop reaction conditions for the introduction of a standard level of carboxymethylation and then to adjust the isoelectric point of the membrane to any desired value by introducing varying amounts of aminoalkyl or other amino-containing groups under controlled reaction conditions as determined by experiment. By way of example, filter paper supports impregnated with solutions of agarose (4% w/v), soaked in aqueous alkali, and cross-linked by treatment with epichlorhydrin (1-chloro-2:3-epoxypropane) may be carboxymethylated by treatment with a solution of sodium chloroacetate (1 M) in sodium hydroxide (1.5 M) for two hours duration. Following this the membranes are aminoalkylated to varying extents by treatment with epichlorhydrin and varying amounts of diethanolamine (0.08 M–0.12 M) under alkaline conditions giving rise to a series of isoelectric membranes over the pH ranges indicated below:

| Ethanolamine molar concentration | Isoelectric pH ($\pm$ 0–1) |
|---|---|
| 0.08 | 4.8 |
| 0.10 | 5.1 |
| 0.12 | 5.5 |

It will be appreciated that isoelectric points on the alkaline side of neutrality may be achieved with the use of more severe aminoalkylation reaction conditions. The membranes produced by the modified method described will thus contain cross-linking groups of formula $-OCH_2CHOH\ CH_2O-$ and substituent groups of formula $-CH_2COOH$ (acid form) and $-OCH_2.CHOH\ CH_2N\ (CH_2CH_2OH)_2$ (basic form).

In an alternative method, ampholytes i.e. substituents containing both acidic and basic groups can be attached to the membrane or membrane-forming substrate material by linking reagents such as epichlorhydrin in an extension of the method described above. Thus an ampholyte such as the reaction product of chloracetic acid and tetraethylene pentamine (a complex mixture of species of varied formulae one of which, for example, has the formula $HOOC.CH_2.NH(CH_2CH_2NH)_4CH_2COOH$) or an ampholyte commercially available under the Trade Mark Ampholine (LKB) may be combined with the membrane material through the reaction with epichlorhydrin in a similar manner to that described above for diethanolamine. By using mixtures of such ampholytes of varying degrees of acidity or basicity the resulting pI of the membrane may be predetermined precisely or within a narrow range of pH. Values of pI over the range pH 4 to 6 are conveniently obtained by this method.

Yet further methods may commend themselves to those skilled in the art and require only brief mention here. For example, charged molecules of higher molecular weight than the above-mentioned reagents may be incorporated physically into the membrane e.g. during casting or chemically linked to a gel activated with cyanogen bromide.

CALIBRATION

Following the general guidelines given above, and with practical experience, it is possible to prepare membranes to a predeterminedd pI value within an approximate range. Successive approximation methods may then be applied, using the electroendosmotic effect with a marker substance e.g. benzyl alcohol, in a test series of membranes set up under practical conditions of electrophoresis. These are repeated until calibration to the required degree of precision is achieved. It will be appreciated that for most purposes it is not required to know the pI of the membrane with absolute precision, because this is often not necessary as a practical matter, and the knowledge of a narrow pH band in which the pI lies will suffice.

ELECTROPHORESIS METHOD

The isoelectric membranes of the present invention, which may be alternatively described as ampholyte membranes, are intended to be used in a graded series of increasing isoelectric point from anode (+electrode) to cathode (−electrode) each membrane separating electrolyte compartments having a pH respectively below the isoelectric point pI of the membrane on its anodic side and above the pI on its cathodic side. The electrolyte pH difference between both sides of each of the successive membranes may be adjusted to suit the purposes of the particular separation being considered; the more gradual this is in the series the more the resolving power of the particular apparatus. Differences in pH of the order of 0.5 units have been found suitable.

The number of membranes involved will also depend on the complexity of the separation. In one of the simpler separations where recovery of only one component is necessary, the others being discarded, the use of two isoelectric membranes will often be sufficient. In most cases more than two will be desirable.

The necessary pH gradient may be created in many ways. One of the most convenient methods uses a series of buffer solutions containing monovalent ions provided by a salt of a strong base and weak acid e.g. sodium acetate (or, alternatively, a salt of a strong acid and weak base or yet again, a salt of a weak acid and weak base), and containing varying amounts of added weak acid (or weak base or both weak acid and weak base). If we consider the use of sodium acetate-acetic acid buffer it will be understood that the bulk of the electric current will be carried through the series of compartments by sodium ions passing progressively from the first compartment (the anodic side of the series) to the last compartment (the cathodic side) and by acetate ions moving in the opposite direction.

The ratios of the sodium ion and acetic acid concentrations in the various compartments are adjusted to give the required pH, so that each isoelectric membrane separates a compartment on its anodic side having a pH lower than its pI from a compartment on its cathodic side having a higher pH. When electricity is passed through the apparatus arrangements must be made to continually restore cations to the first compartment (A) and anions to the last compartment (B) and at the same time to remove anions from compartment A and cations from compartment B. This is most easily done by adjusting the concentrations of the buffer salts in compartments A and B such that when equal volumes of liquid are circulated from A to B and from B to A at a rate determined by and proportional to the electric current flowing through the cell, the net transfer of buffer by circulation equals the net transfer by the electric current. There are many other possible ways of maintaining the concentrations in compartments A and B. For instance counterflow of ions can be performed electrically or fresh buffer solution can be continually passed through A and B and then to waste. The use of this method, involving one singly charged anion and one singly charged cation together with uncharged molecules of acid or base or both is particularly suitable where only a small range of isoelectric points is required. For a larger range use may be made of acids or bases which have multiple ionised forms having individual values not widely separated e.g. mellitic acid. This particular technique however involves the use of auxiliary electrodes in the various compartments.

Another method of establishing the pH gradient is by means of a mixture of carrier ampholytes which migrate in the electrical field until they reach a compartment having a pH equal to their isoelectric point wherein they remain stationary. This is a more costly method but avoids the need for arrangements for counterflow described above when simple buffers are used.

ELECTROPHORESIS APPARATUS

It will be appreciated from the foregoing that the present invention also comprises a multi-diaphragm apparatus for isoelectric focussing containing a series of isoelectric membranes arranged in sequence of isoelectric point between the anode and cathode, the isoelectric point becoming increasingly alkaline towards the cathode. The membranes in multi-diaphragm apparatus of the kind described may be arranged in any desired configuration, for example either as a horizontal series of vertically disposed membranes arranged side by side and separated by the customary spacers or as a vertical series e.g. in a nesting arrangement of membranes supported one above the other in the vertical direction. One particularly convenient form involves membranes in sheet form resting one above the other and suitably spaced apart and arranged for gravity flow of the electrolytes through the various compartments from one end of the system to the other. With membranes in extended sheet form as described it will be necessary to provide sealing along two opposite edges of the membranes in order to confine the liquid in the apparatus and to direct it in the desired direction through the apparatus. In all these cases it is a particularly attractive and preferred feature of the invention to provide separate pumping and cooling arrangements for each of the electrolyte circuits for the various compartments.

Preferably the anode and cathode of the system are located in appropriate electrolyte baths at opposite ends of the apparatus each such bath being separated from the membrane system by means of an ion exclusion membrane. At the anode end the ion exclusion membrane will be a highly negatively charged cation exchanger whereas at the cathode end the ion exclusion membrane will be a highly positively charged anion exchanger. By this means current is led into the apparatus at the anode by means of hydrogen ions only, and at the cathode end there is a corresponding counterflow of hydroxyl ions.

Figure 2:
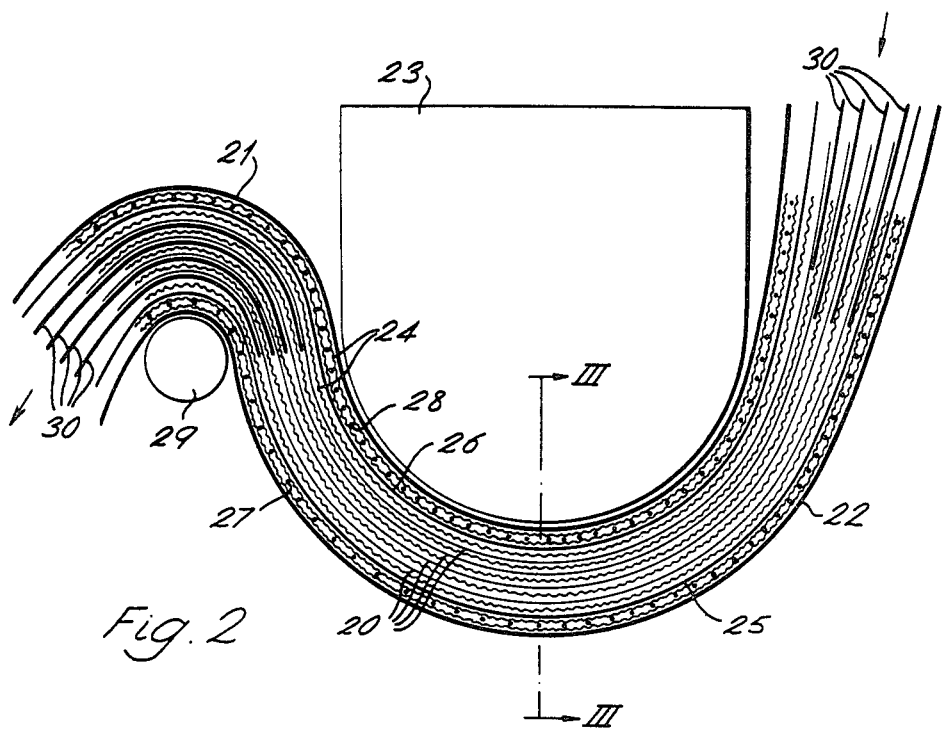
Figure 3:
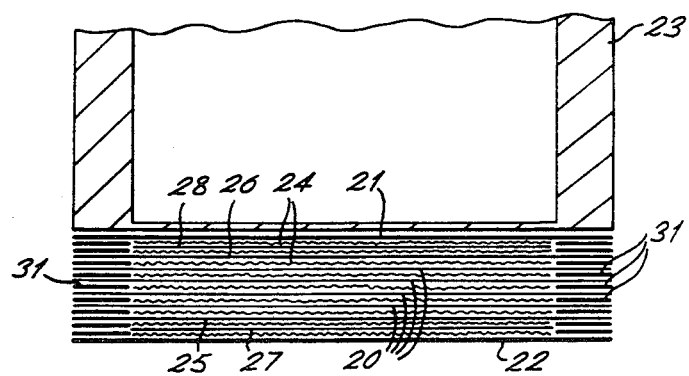

The invention will now be further described with reference to the accompanying drawings of which:

FIG. 1 is a schematic view of the principle of the electrophoresis apparatus of the invention, FIG. 2 is a sectional view of a practical arrangement of nesting membranes taken in the direction of electrolyte flow, and FIG. 3 is a transverse sectional view of the apparatus of FIG. 2 taken across the direction of electrolyte flow.

Referring now to FIG. 1 the apparatus consists of a stack of isoelectric membranes 1 defining between them compartments 2 into which the components of a mixture are to be separated. Four such membranes 1 are shown defining three compartments 2 but it will be understood that the system can be extended indefinitely in length. At opposite ends of the system are the electrodes. At the left-hand end a lead peroxide anode 3 is immersed in a dilute sulphuric acid compartment 4 and is electrically connected to the stack by means of a cation exchange membrane 5 so that all current is transported by hydrogen ions. The membrane 5 is separated from the first isoelectric membrane 1 by means of a compartment 6. At the other end a mild steel cathode 7 is immersed in a dilute sodium hydroxide compartment 8 and is electrically connected to the stack by means of a highly positively charged anion exchange membrane 9 so that all current at this end of the apparatus is transported by hydroxyl ions. Hence only the elements of water are passed from the electrode compartments to the rest of the stack during passage of current. The membrane 9 is separated from the last isoelectric membrane 1 of the system by means of a compartment 10.

The apparatus thus comprises three separator compartments 2 with two additional compartments 6 and 8 and into all these compartments buffers at appropriate pH are introduced. By gravity or pumping devices a continuous flow is established in all compartments by circuits shown diagrammatically at 11 which include heat exchangers (not shown). A two-directional counterflow of electrolyte is arranged between compartment 6 and compartment 10 to restore electrolyte balance necessary because of continuous depletion of anions and cations as electric current passes.

Referring now to FIGS. 2 and 3, a nesting arrangement of ampholyte membranes 20 supported between strong plastic sheets 21 and 22 are mounted around a support member 23. The membranes 20 are separated by means of gauze layers 24 and outside the four membrane sandwich so formed there are positioned an outer anion exchange membrane 25 and an inner cation exchange membrane 26. Outside these are the electrodes, the cathode 27 being outermost and the anode 28 being innermost, both of which are similarly protected by gauzes.

The generally trough-shaped arrangement of membranes passes over a weir 29 so positioned that electrolyte flow through the system can be by means of gravity. Introduction of electrolyte from the right-hand end of the system as shown and withdrawal of electrolyte from the left-hand part of the system as shown is achieved by means of separator devices 30 also of strong plastic film which diverge outwardly from the relatively narrow channel in between adjacent membranes 20 so as to facilitate introduction and withdrawal of electrolyte. As seen in FIG. 3 the flow of electrolyte is confined within the sandwich by means of gasket sealing strips 31 extending along opposite longitudinal edges of the system. Fluid tightness is achieved by suitable clamping means (not shown). Typical membranes for use in the apparatus may be made by chemical methods as described in the following Examples.

EXAMPLE 1

Hardened filter papers (Whatman grade 541) are soaked in hot aqueous agarose (2%–8% w/v) and the surplus agarose removed by pressing the paper between two warm glass plates. After the impregnated papers have cooled they are soaked for one hour in aqueous sodium hydrode (2.5 M) and then after blotting lightly they are suspended overnight in xylene containing epichlorhydrin (1% v/v). This cross-liks the gel and strengthens it for subsequent treatment. The membranes are then soaked for one hour in sodium hydroxide (2.5 M) and immersed for two hours in an alkaline solution of sodium chloroacetate freshly prepared my mixing equal volumes of sodium hydroxide solution (5.0 M) and chloroacetic acid (2 M). After two hours the carboxylated membranes are rinsed in sodium hydroxide solution (2.5 M) and then soaked for two hours in 2.5 M sodium hydroxide containing diethanolamine (0.08–0.12 M). After two hours the membranes are blotted lightly and suspended overnight in xylene containing epichlorhydrin (8% v/v) during which time the epichlorhydrin reacts with the gel and links the diethanolamine to the gel. This procedure gives membranes with isoelectric point between pH 4.8 and 5.5.

EXAMPLE 2

The membrane is a filter paper impregnated with 4% agarose gel. It is soaked for 1.5 hours in a solution prepared from one or a mixture of the following reagents.

Acidic reagent
  LKB Ampholine carrier ampholyte ph range 3.5–5, code 1809-111.

Basic reagent
  A solution of chloracetic acid (47.25 g) in water (100 ml) is added slowly with stirring to a solution of technical grade tetraethylene pentamine (90 ml) in water (100 ml). When addition is complete the solution is diluted with water to 300 ml.

The solution is prepared by adding about 5 ml of Acidic Reagent or Basic Reagent or a total of about 5 ml of a mixture of these Reagents to 10% aqueous sodium hydroxide (40 ml).

After soaking the membrane is removed, lightly blotted, and then transferred to a solution (8% w/v) of epichlorhydrin in toluene and stood overnight.

Typical pI values obtained by varying the amounts of reagent used are as follows:

| Membrane | Acidic Reagent (ml) | Basic Reagent (ml) | pI |
|---|---|---|---|
| A | 5 | 0 | 4–4.5 |
| B | 4 | 1 | 4.5–5.0 |
| C | 4 | 1.05 | 5.0–5.5 |
| D | 4 | 1.10 | 5.5–6.0 |
| X | 0 | 5 | above 10 |
| E (control) | 0 | 0 | — |

EXAMPLE 3

The use of membranes A, B, C and D prepared as described in Example 2 and a comparison with control membrane E (non-isoelectric) is demonstrated by the following experiments. For convenience the method is related to the scheme shown in FIG. 1 of the drawings.

The experiments were performed in a five compartment apparatus. The area of the membranes was 26.4 cm$^2$ and the current at the start of each experiment was approximately 1.25 A i.e. 47 mA/cm$^2$. The contents of each compartment 2 were circulated by means of pumps through external coolers and reservoirs to form 5 separate circuits. The liquids in the end compartments i.e. 6 and 10 were circulated at a rate of about 500 ml/min, whilst the liquids in the intermediate compartments 2 were circulated at approximately 100 ml/min. The buffer solution used was sodium pivalate.

The compositions and amounts of the solution in each circuit are tabulated below. For convenience the compartments from left to right in FIG. 1 (i.e. 6 to 10) are referred to as circuits 1 to 5 respectively. In this Example, circuits 1 and 5 have such large volumes that compositional changes are insignificant and therefore the two-directional flow between them is omitted.

| Circuit | 1 | 2 | 3 | 4 | 5 |
|---|---|---|---|---|---|
| Volume Liters | 10 | 0.45 | 0.45 | 50.0 | 5 |
| pH (calculated) | 4.0 | 4.5 | 5.0 | 5.5 | 6.0 |
| Ionic Concentration mM Na$^+$ | 11.4 | 6.7 | 6.7 | 6.7 | 67.0 |

In the first experiment Membrane A was placed between circuits (1) and (2), membrane B was placed between (2) and (3), membrane C was placed between (3) and (4), and membrane D between circuits (4) and (5). A mixture of bovine serum Albumin (1 g) and horse heart cytochrome approx. (0.15 g) was dissolved in the solution circulating in circuit 4. The analytical results are shown in Table II.

TABLE II

| | | 1 | 2 | 3 | 4 | 5 |
|---|---|---|---|---|---|---|
| Time Minutes 0 | pH | 4.0 | 4.55 | 5.05 | 5.50 | 6.05 |
| | Volume ml. | 10,000 | 450 | 450 | 450 | 50,000 |
| | Conductivity (ohms$^{-1}$cm$^{-1}$ × 10$^6$) | 19.5 | 13.5 | 13.5 | 13.5 | 100.5 |
| | Conc. BSA | — | 0 | 0 | 2.2 | — |
| | Conc. Cytochrome Mg/ml | — | 0 | 0 | 0.325 | — |
| Time Minutes 15 | pH | — | 4.55 | 5.05 | 5.50 | — |
| | Volume ml. | — | 450 | 450 | 450 | — |
| | Conductivity (ohms$^{-1}$cm$^{-1}$ × 10$^6$) | — | — | — | — | — |
| | Conc. BSA | — | 0 | 0.48 | — | — |
| | Conc. Cytochrome Mg/ml | — | 0 | 0 | 0.22 | — |
| Time Minutes 30 | pH | — | 4.55 | 5.08 | 5.50 | — |
| | Volume ml. | — | 445 | 450 | 450 | — |
| | Conductivity (ohms$^{-1}$cm$^{-1}$ × 10$^6$) | — | 13.0 | — | — | — |
| | Conc. BSA Mg/ml | — | 0 | 0.91 | — | — |
| | Conc. Cytochrome MG/ml | — | 0 | 0 | 0.15 | — |
| Time Minutes 45 | pH | 3.95 | 4.55 | 5.13 | 5.50 | 6.2 |
| | Volume ml. | — | 445 | 450 | 450 | — |
| | Conductivity (ohms$^{-1}$cm$^{-1}$ × 10$^6$) | 17.5 | 12.0 | 14 | 13.5 | 101.4 |
| | Conc. BSA Mg/ml | — | 0 | 1.11 | — | — |
| | Conc. Cytochrome Mg/ml | — | 0 | 0 | 0.12 | — |

This Table demonstrates a progressive transference of bovine serum albumin from circuit 4 to circuit 3 and progressive reduction of the cytochrome component in circuit 4. The cytochrome transfers to circuit 5 which is of such large volume as to make analysis difficult. The stable conditions of pH and conductivity due to insignificant electroendosmosis in this experiment are clearly apparent.

In contrast Table III shows results obtained when the membrane C between circuits (3) and (4) is substituted by the control membrane E.

TABLE III

| | | 1 | 2 | 3 | 4 | 5 |
|---|---|---|---|---|---|---|
| Time Minutes 0 | pH | 4.0 | 4.50 | 5.01 | 5.55 | 6.05 |
| | Volume ml | 10,000 | 450 | 450 | 450 | 50,000 |
| | Conductivity (ohms$^{-1}$cm$^{-1}$ × 10$^6$) | 18.5 | 13.5 | 13.5 | 13.6 | 101.5 |
| | Conc. BSA Mg/ml | — | 0 | 0 | 2.2 | — |
| | Conc. Cytochrome Mg/ml | — | 0 | 0 | 0.23 | — |
| Time Minutes | pH | — | 4.50 | 5.00 | 5.45 | — |
| | Volume ml. | — | 450 | 425 | 475 | — |

TABLE III-continued

|  |  | 1 | 2 | 3 | 4 | 5 |
|---|---|---|---|---|---|---|
| 15 | Conductivity (ohms$^{-1}$cm$^{-1}$ × 10$^6$) | — | — | — | — | — |
|  | Conc. BSA Mg/ml | — | 0 | 0 | — | — |
|  | Conc. Cytochrome Mg/ml | — | 0 | 0 | 0.16 | — |
| Time Minutes 30 | pH | 3.95 | 4.45 | 4.95 | 5.35 | 6.01 |
|  | Volume ml. | — | 440 | 385 | 505 | — |
|  | Conductivity (ohms$^{-1}$cm$^{-1}$ × 10$^6$) | 16 | 11.5 | 5.0 | 26 | 100.6 |
|  | Conc. BSA Mg/ml | — | 0 | 0 | — | — |
|  | Conc. Cytochrome Mg/ml | — | 0 | 0 | 0.11 | — |

In Table III the large endosmosis effect is shown by the increase of volume in circuit 4 and its decrease in circuit 3. The endosmotic effect opposes the passage of the albumen to such an extent that none passes into circuit 3. The pH drops continually in circuit 4 due to passage of bulk fluid from circuit 3. The conductivity, which is equal in circuits 2, 3 and 4 at the start of the separation, is dramatically altered in these circuits by the 30 minute stage. It was necessary to abandon the experiment at this point.

We claim:

1. An electrophoresis membrane for use in electrophoresis according to the method of isoelectric focusing in which substances are transported into and out of the membrane across the thickness thereof, said membrane having attached to it acidic and basic groups in such relative amounts as to confer on the membrane a buffering capacity at a specific pH or over a specific narrow pH range at or in which the membrane is isoelectric whereby the tendency for electroendosmosis to occur during electrophoresis is reduced.

2. A membrane according to claim 1 being a gel membrane.

3. A membrane according to claim 1, being a chemically treated agarose or polyacrylamide gel.

4. A membrane according to claim 1, being a supported membrane.

5. A membrane according to claim 1, comprising ampholyte molecules attached to a substrate.

6. A membrane according to claim 5, in which the ampholyte molecules are chemically attached to the substrate.

7. A membrane according to claim 6, in which the attachment is by means of an intermediate linking group.

8. A membrane according to claim 1, having an isoelectric point in the range pH 4 to 6.

9. A membrane electrophoresis apparatus for isoelectric focussing comprising a series of membranes according claim 1, arranged in sequence of increasing isoelectric points towards the cathode (negative electrode) and means for establishing a series of circulating electrolyte zones having a pH gradient of increasing pH in the same direction.

10. Apparatus according to claim 9, comprising means for mounting membranes in a generally vertical series.

11. Apparatus according to claim 10, in which the membranes are in sheet form and arranged in a nesting configuration with edge sealing.

12. Apparatus according to claim 11, in which electrolyte flow through the compartments between the membranes is by gravity.

13. Apparatus according to claim 9, in which each electrolyte zone in the pH gradient is provided with cooling means.

14. Apparatus according to claim 9, having an anode in an acidic compartment separated from the membrane series by an anion exclusion membrane so that electricity is carried through the latter exclusively by hydrogn ions.

15. Apparatus according to claim 14 in which the anode is lead peroxide in dilute sulphuric acid.

16. Apparatus according to claim 9, having a cathode in an alkaline compartment separated from the membrane series by a cation exclusion membrane so that electricity is carried through the latter exclusively by hydroxyl ions.

17. Apparatus according to claim 16, in which the cathode is mild steel in a dilute solution of an alkali metal hydroxide.

* * * * *

UNITED STATES PATENT AND TRADEMARK OFFICE
CERTIFICATE OF CORRECTION

PATENT NO. : 4,243,507
DATED : January 6, 1981
INVENTOR(S) : ARCHER JOHN PORTER MARTIN ET AL It is certified that error appears in the above-identified patent and that said Letters Patent are hereby corrected as shown below:

In the heating insert

-- Foreign Application Priority Data

June 15, 1977 - United Kingdom - 25043/77 --.

Signed and Sealed this

Nineteenth Day of May 1981

[SEAL]

Attest:

RENE D. TEGTMEYER

Attesting Officer    Acting Commissioner of Patents and Trademarks